United States Patent [19]

Wandell

[11] Patent Number: Plant 7,033

[45] Date of Patent: Sep. 19, 1989

[54] *PYRUS BETULAEFOLIA* 'SOUTHWORTH'

[76] Inventor: Willet N. Wandell, R.R. 1, Box 286, Oquawka, Ill. 61469

[21] Appl. No.: 251,860

[22] Filed: Oct. 3, 1988

[51] Int. Cl.[4] ..... A01H 5/00

[52] U.S. Cl. ..... Plt./36

[58] Field of Search ..... Plt./36

[56] References Cited

PUBLICATIONS

Rehder, A., (1960) "Rosaceae: *Pyrus:* 12. *P. betulaefolia*", *Manual of Cultivated Trees and Shrubs,* The Macmillan Co., N.Y., p. 405.

Bailey, L. H., (1935) "*Pyrus:* 14. *P. betulaefolia*", *The Standard Cyclopedia of Horticulture,* The Macmillan Co., N.Y., p. 2809.

*Primary Examiner*—James R. Feyrer

[57] ABSTRACT

A new and distinct *Pyrus betulaefolia* pear tree which is superior in mature leaf glossiness, coloration, a longer petiole and placement, when compared to other trees of the specie. The new trees named 'Southworth' has strongly ascending branches which develop into a tree of symmetrical, ovoid crown.

2 Drawing Sheets

This new variety of *Pyrus betulaefolia* pear was discovered by me growing in a cultivated area in northern Illinois. The new variety had a vigorous upright growth habit with light green glossy foliage following new leaves of a whitish silvery cast. The tree was outstanding because of flexible longer petioles which permit movement throughout the crown with the slightest breeze much like the leaf movement in Quacking Aspen (*Populus tremuloides*). Further, this attractive tree produced white flowers in abundance but only a small amount of fruit of a relatively small size (⅜" diameter). I have 500 asexually produced trees of this selection by chip budding in my nursery at Oquawka, Ill., all of which exhibit the superior growing qualities of the parent plant.

SUMMARY OF INVENTION

A new and distinct cultivar of *Pyrus betulaefolia* with an upright growth habit, glossy pale green leaves which move in the breeze longer than the species petioles, abundant white flowers and limited small ⅜" size fruit.

BRIEF DESCRIPTION OF DRAWINGS

FIG. 3 is a photographic view of the blossoms and leaves.

FIG. 4 is a photographic view of the summer foliage.

DESCRIPTION OF THE NEW PLANT

Figure 1:
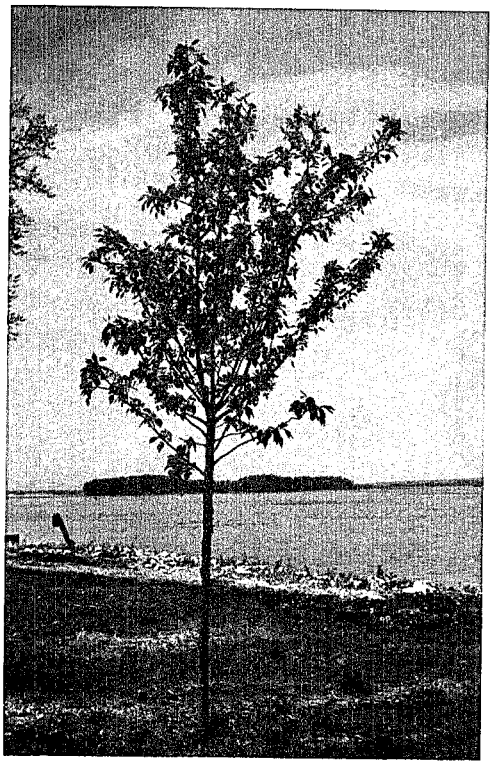
FIG. 1 is a photographic view of my new variety as it appears with foliage.
Figure 2:
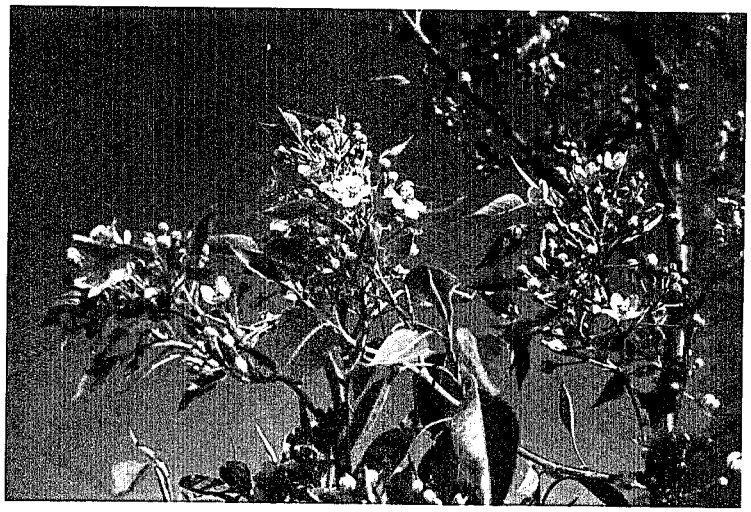
FIG. 2 is a photographic view of my new variety as it appears in flower bud and bloom.

The following is a detailed description of my new variety of *Pyrus betulaefolia* pear with color designations according to the R.H.S. Colour Chart published by The Royal Horticultural Society of London, England and the stated observations having been made on trees growing in Lisle and Oquawka, Ill. by the applicant and found to distinguish from the species.

Origin: Seedling growing under cultivated conditions.

Parentage and classification: Variety of *Pyrus betulaefolia.*

Form: Medium sized tree.

Habit: Deciduous tree with a one trunk and a single straight leader, the main branches strongly ascending, forming a symmetrical ovoid crown.

Twigs: Slender, the new growth of the year on both long shoots from terminal buds and short spurs lateral on older twigs; first year twigs 1.5–2 mm in diameter and tomentose with whitish hairs, second year twigs 2–3.5 mm in diameter and glabrous; spurs with crowded remnants of leaf bases at the base, the individual leaf scars usually not readily discernible.

Winterbuds: Narrowly tapering ovoid, reddish brown, 4–5 mm long, with ca. 8 exposed bud scales, the scales with acuminate and tomentose apices.

Bark: Gray-brown with cinnamon colored underbark, the flat-topped elongate scales broken by longitudinal fissures.

Leaves: Alternately arranged, deciduous, simple; blades ovate or slightly rhomboid, 5–7 cm long and 2.5–4 cm broad, the apices acuminate, the margins sharply serrate with somewhat spreading teeth, the bases broadly cuneate to nearly rounded; young leaves densely tomentose above and below with hairs initially tawny becoming whitish; mature leaves glabrous above and below, the upper surfaces bright green and glossy (RHS 138A), the lower surfaces paler (RHS 146B) dull; petioles elongate, 6.5 cm long, slender, 0.5–0.8 mm in diameter, spreading-tomentose; stipules very small, 1 mm long, caducous. Leaves are much less flat than normal, mature leaves having a shape approaching a crescent in profile. The leaves have a unique V-shape to U-shape in cross-section with the top leaf surface curving upwardly progressively with increased distance from the central vein to result in a distinct marginal curl. Leaves have slight but distinct undulation. Fall color is not outstanding. After frost the leaves turn a bright yellow before dropping.

Flowers: Perfect, white, 2 cm across; inflorescences condensed racemes, 8–12 flowered, the pedicels tomentose, to 2.5 cm long; petals 5, broadly ovoid, 10 mm long and 7 mm wide, the tips obtuse, the margins entire; calyx lobes lanceolate, 5 mm long, the tips tapering, the margins with glandular teeth; stamens ca. 20; styles 2, free, exceeding the stamens; ovary inferior, 2-loculate, each locule with 2 ovules. Full bloom is not attained until leaves are approaching a fully expanded state; being later in blooming relative to leaf expansion than is typical of the specie. Bloom, although heavy, does not result in a heavy set of fruit.

Fruit: Pomes, small, 1 cm in diameter, globose, greenish-brown, the surface marked with many small circular lenticels, the calyx deciduous, the flesh containing abundant stone cells.

I claim:

1. A new and distinctive variety of *Pyrus betulaefolia* named 'Southworth' as described and illustrated herein that differs from all other varieties by the unique combination of: (1) silvery juvenile foliage; (2) mature leaves bright green and glossy above, paler and dull below; (3) long, slender petioles so that leaves flutter in a slight breeze; (4) showy white flowers in spring as the silvery leaves unfold; (5) lack of messy fruits; (6) strongly ascending branch angles; (7) neat, symmetrical ovoid crown; (8) and plants extremely hardy; (9) leaves much less flat than normal; (10) mature leaves having a shape approaching a crescent in profile; (11) leaves having a unique V-shape to U-shape in cross-section with the top leaf surface curving upwardly progressively with increased distance from the central vein to result in a distinct marginal curl. Leaves have slight but distinct undulation. Full bloom is not attained until leaves are approaching a fully expanded state; later in blooming relative to leaf expansion than is typical of the specie.

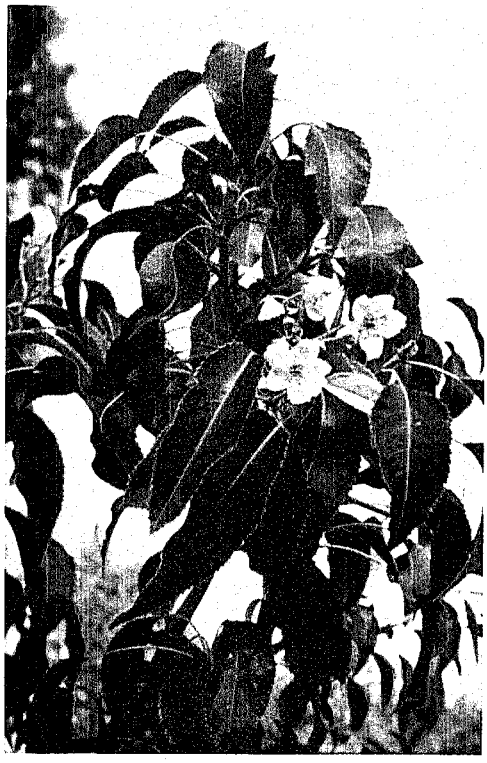
FIG. 3
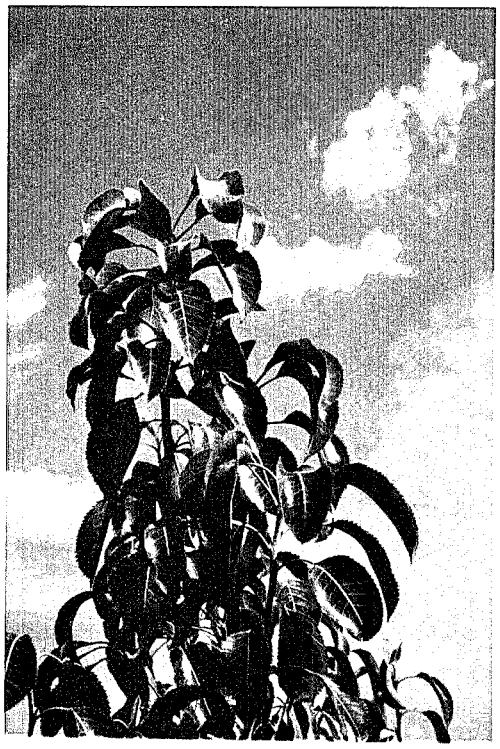

* * * * *